US012589222B2

(12) United States Patent (10) Patent No.: US 12,589,222 B2

Schlesinger (45) Date of Patent: Mar. 31, 2026

(54) DEVICES, SYSTEMS, AND METHODS FOR ANCHORING ACTUATION WIRES TO A STEERABLE INSTRUMENT

(71) Applicant: Intuitive Surgical Operations, Inc., Sunnyvale, CA (US)

(72) Inventor: Randall L. Schlesinger, San Mateo, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 1328 days.

(21) Appl. No.: 17/317,176

(22) Filed: May 11, 2021

(65) Prior Publication Data

US 2021/0268235 A1 Sep. 2, 2021

Related U.S. Application Data

(63) Continuation of application No. 15/542,850, filed as application No. PCT/US2016/012578 on Jan. 8, 2016, now Pat. No. 11,033,716.

(Continued)

(51) Int. Cl.
A61M 25/01 (2006.01)
A61B 17/00 (2006.01)
(Continued)

(52) U.S. Cl.
CPC ......... A61M 25/0147 (2013.01); A61B 34/35 (2016.02); A61B 34/74 (2016.02);
(Continued)

(58) Field of Classification Search
CPC ........ A61M 25/0147; A61M 2025/015; A61B 34/74; A61B 34/35; A61B 2034/304;
(Continued)

(56) References Cited

U.S. PATENT DOCUMENTS

| | | | | |
|---|---|---|---|---|
| 4,846,573 A | * | 7/1989 | Taylor ................. | A61B 1/0055 |
| | | | | 356/241.4 |
| 5,372,587 A | * | 12/1994 | Hammerslag ..... | A61M 25/0144 |
| | | | | 604/95.04 |

(Continued)

FOREIGN PATENT DOCUMENTS

WO WO-2008131303 A2 * 10/2008 ............. A61B 1/009

OTHER PUBLICATIONS

Affix: Definition of Affix by Merriam-Webster, http://www.merriam-webster.com/dictionary/affix, Accessed Feb. 14, 2020.

(Continued)

*Primary Examiner* — Bhisma Mehta
*Assistant Examiner* — Mark A Igel
(74) *Attorney, Agent, or Firm* — Haynes & Boone, LLP.

(57) ABSTRACT

A pull wire attachment system for a minimally invasive medical instrument comprises an anchoring element fixedly attached to the medical instrument. The anchoring element has a first outer diameter. The system also includes a pull wire assembly comprising an elongate pull wire having a proximal end and a distal end and a securing element coupled to the distal end of the pull wire. The securing element includes a second outer diameter sized smaller than the first outer diameter of the anchoring element. The securing element is coupled to the anchoring element to prevent proximal translation of the distal end of the pull wire along a longitudinal axis of the medical instrument past the anchoring element.

20 Claims, 6 Drawing Sheets

Related U.S. Application Data

(60) Provisional application No. 62/102,317, filed on Jan. 12, 2015.

(51) Int. Cl.
A61B 34/00 (2016.01)
A61B 34/35 (2016.01)

(52) U.S. Cl.
CPC ............... *A61B 2017/00309* (2013.01); *A61B 2017/00323* (2013.01); *A61M 2025/015* (2013.01)

(58) Field of Classification Search
CPC .... A61B 2034/741; A61B 2017/00203; A61B 2017/00207; A61B 2017/00309; A61B 2017/00323; A61B 1/0056; A61B 1/0057
See application file for complete search history.

(56) References Cited

U.S. PATENT DOCUMENTS

| | | | | |
|---|---|---|---|---|
| 5,395,329 | A * | 3/1995 | Fleischhacker ... | A61M 25/0136 604/95.04 |
| 5,472,017 | A * | 12/1995 | Kovalcheck ...... | A61M 25/0136 138/120 |
| 6,183,435 | B1 * | 2/2001 | Bumbalough .... | A61M 25/0136 604/95.01 |
| 6,464,699 | B1 * | 10/2002 | Swanson .......... | A61B 17/00234 606/41 |
| 7,316,681 | B2 | 1/2008 | Madhani et al. | |
| 8,540,696 | B2 * | 9/2013 | McDaniel ............ | A61M 25/00 604/95.04 |
| 9,259,274 | B2 * | 2/2016 | Prisco ................... | A61B 34/37 |
| 9,452,276 | B2 * | 9/2016 | Duindam .......... | A61M 25/0113 |
| 2004/0059288 | A1 * | 3/2004 | Webler .............. | A61M 25/0147 604/95.04 |
| 2007/0005008 | A1 * | 1/2007 | Honebrink ........ | A61M 25/0147 604/95.04 |
| 2007/0156116 | A1 * | 7/2007 | Gonzalez ............... | A61B 1/008 604/528 |
| 2008/0218770 | A1 * | 9/2008 | Moll .................... | A61G 7/0503 356/614 |
| 2008/0275300 | A1 * | 11/2008 | Rothe ................ | A61B 5/02007 600/129 |
| 2009/0254083 | A1 * | 10/2009 | Wallace ............. | A61B 18/1492 606/41 |
| 2013/0096377 | A1 * | 4/2013 | Duindam .............. | A61B 10/02 600/104 |
| 2013/0281925 | A1 * | 10/2013 | Benscoter ........... | A61B 1/0125 604/95.04 |
| 2014/0148673 | A1 * | 5/2014 | Bogusky ................ | A61B 34/30 604/95.04 |
| 2014/0194814 | A1 | 7/2014 | Benscoter et al. | |
| 2018/0001058 | A1 | 1/2018 | Schlesinger | |

OTHER PUBLICATIONS

Anchor: Definition of Anchor by Merriam-Webster, http://www. merriam- webster.com/dictionary/anchor, Accessed Feb. 14, 2020.
Crimp: Definition of Crimp by Merriam-Webster, http://www. merriam- webster.com/dictionary/crimp, Accessed Feb. 14, 2020.
International Preliminary Report on Patentability for Application No. PCT/US2016/012578, mailed on Jul. 27, 2017, 6 pages.
International Search Report and Written Opinion for Application No. PCT/US2016/012578, mailed on Apr. 21, 2016, 7 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

DEVICES, SYSTEMS, AND METHODS FOR ANCHORING ACTUATION WIRES TO A STEERABLE INSTRUMENT

RELATED APPLICATIONS

This patent application is the continuation application of U.S. patent application Ser. No. 15/542,850, filed Jul. 11, 2017, which is the U.S. national phase of International Application No. PCT/US2016/012578, filed Jan. 8, 2016, which designated the U.S. and claims priority to and the benefit of the filing date of U.S. Provisional Patent Application 62/102,317, entitled "DEVICES, SYSTEMS, AND METHODS FOR ANCHORING ACTUATION WIRES TO A STEERABLE INSTRUMENT," filed Jan. 12, 2015, all of which are incorporated by reference herein in their entirety.

FIELD

The present disclosure is directed to devices, systems, and methods for anchoring actuation or pull wires to a steerable medical instrument.

BACKGROUND

Minimally invasive medical techniques are intended to reduce the amount of tissue that is damaged during medical procedures, thereby reducing patient recovery time, discomfort, and harmful side effects. Such minimally invasive techniques may be performed through natural orifices in a patient anatomy or through one or more surgical incisions. Clinicians may insert medical tools through these natural orifices or incisions to reach a target tissue location. Medical tools include instruments such as therapeutic instruments, diagnostic instruments, and surgical instruments. To reach the target tissue location, a minimally invasive medical tool may navigate natural or surgically created passageways in anatomical systems such as the lungs, the colon, the intestines, the kidneys, the heart, the circulatory system, or the like.

Minimally invasive medical tools include steerable catheters and other flexible medical instruments. Traditional catheters include solid actuation or pull wires that are directly attached to an anchor structure (e.g., an anchor ring) located on a distal portion of the catheter via a welding method, such as laser welding or soldering. Attachment through laser welding, however, can be difficult because solid pull wires tend to be high tensile strength wires that have been work hardened, and the heat from the laser weld tends to anneal the wire, thus weakening the strength of the wire. Another potential problem with solid pull wires having high tensile strength is that they are stiff when bent, which adds to the overall bending force required to articulate the distal end of the catheter. This problem is compounded when multiple wires are used, as may be necessary to articulate the catheter in multiple directions. Additionally, the high bending stiffness of traditional solid pull wires may decrease safety due to higher buckle forces.

To alleviate the problems associated with solid pull wires, cable metal actuation wires may be used instead (e.g., to decrease the bending stiffness). However, it can be difficult to attach cable metal pull wires at their distal ends while maintaining a low device profile or low circumferential outline at the attachment point. Cable metal pull wires are frequently attached to flexible medical instruments by first attaching a securing component, such as a crimp, to a distal end of the cable metal pull wire and then mechanically locking the securing component to an anchor element on the instrument. Mechanical locking mechanisms, however, generally increase the circumferential profile of the device and can be more intrusive during medical procedures.

Thus, it is desirable to provide devices, systems, and methods that enable the effective attachment of actuation wires to medical instruments with lower bending stiffness while preserving the low overall circumferential profile of the instrument. The devices, systems, and methods disclosed herein overcome one or more of the deficiencies of the prior art.

SUMMARY

In one embodiment, a pull wire attachment system for a minimally invasive medical instrument comprises an anchoring element fixedly attached to the medical instrument. The anchoring element has a first outer diameter. The system also includes a pull wire assembly comprising an elongate pull wire having a proximal end and a distal end and a securing element coupled to the distal end of the pull wire. The securing element includes a second outer diameter sized smaller than the first outer diameter of the anchoring element. The securing element is coupled to the anchoring element to prevent proximal translation of the distal end of the pull wire along a longitudinal axis of the medical instrument past the anchoring element. Additional aspects, features, and advantages of the present disclosure will become apparent from the following detailed description.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

DETAILED DESCRIPTION

Figure 1:
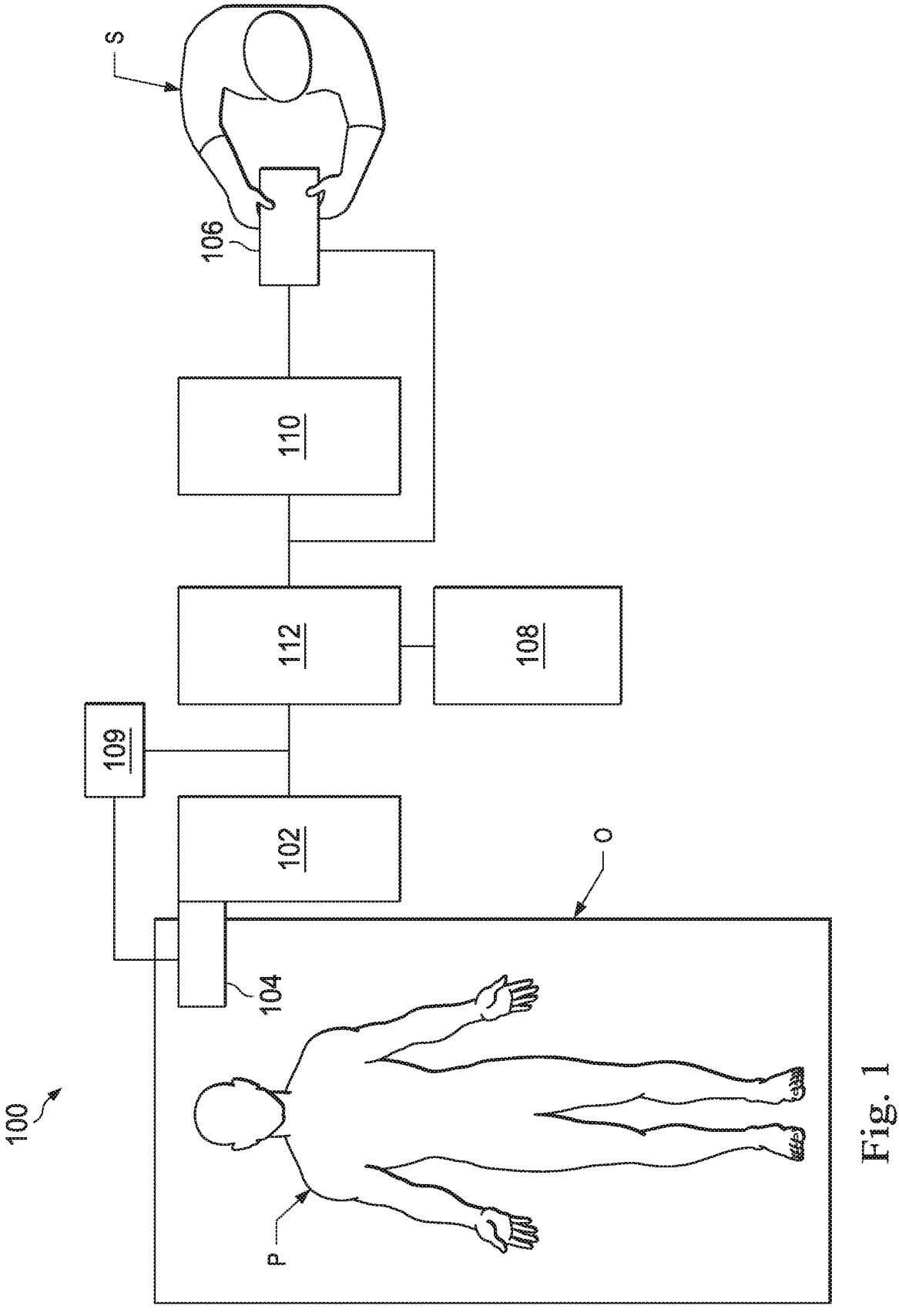
FIG. 1 is a diagram showing an illustrative teleoperational medical system according to one embodiment of the present disclosure.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. In the following detailed description of the aspects of the invention, numerous specific details are set forth in order to provide a thorough understanding of the disclosed embodiments. However, it will be obvious to one skilled in the art that the embodiments of this disclosure may be practiced without these specific details. In other instances well known methods, procedures, components, and circuits have not been described in detail so as not to unnecessarily obscure aspects of the embodiments of the invention.

Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. In addition, dimensions provided herein are for specific examples and it is contemplated that different sizes, dimensions, and/or ratios may be utilized to implement the concepts of the present disclosure. To avoid needless descriptive repetition, one or more components or actions described in accordance with one illustrative embodiment can be used or omitted as applicable from other illustrative embodiments. For the sake of brevity, the numerous iterations of these combinations will not be described separately. For simplicity, in some instances the same reference numbers are used throughout the drawings to refer to the same or like parts.

The embodiments below will describe various instruments and portions of instruments in terms of their state in three-dimensional space. As used herein, the term "position" refers to the location of an object or a portion of an object in a three-dimensional space (e.g., three degrees of translational freedom along Cartesian X, Y, Z coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

It will be appreciated that the terms "proximal" and "distal" are used herein with reference to a clinician manipulating an end of an instrument extending from the clinician to a surgical site. The term "proximal" refers to the portion of the instrument closer to the clinician, and the term "distal" refers to the portion of the instrument further away from the clinician and closer to the surgical site. For conciseness and clarity, spatial terms such as "horizontal," "vertical," "above," and "below" may be used herein with respect to the drawings. However, surgical instruments are used in many orientations and positions, and there terms are not intended to be limiting and absolute.

The present disclosure relates generally to devices and methods for anchoring or attaching actuation cables (e.g., pull wires) to flexible medical instruments such as steerable catheters. In general, such actuation cables or pull wires enable the articulation of at least a distal portion of a catheter. The embodiments described in the present disclosure allow for the attachment of pull wires formed from desirable materials while maintaining a low overall circumferential profile of the medical instrument. Several different embodiments of attachment systems for coupling pull wires to catheters are described. In one aspect, the pull wire attachment system comprises a pull wire coupled to a securing element, which is then affixed (e.g., via soldering or laser welding) to an anchoring element on the medical instrument. In some embodiments, the pull wire attachment system may be soldered (via the securing element) directly onto an anchoring element on a distal portion of the instrument body. For example, a pull wire may be coupled to a securing element, such as, by way of non-limiting example, a cylindrical crimp, and the securing element may be soldered to a lateral surface of an anchoring element, such as, by way of non-limiting example, an anchor ring, a distal metal tip, and/or a shape memory flexure, on the instrument body. In some embodiments, the securing element may be sized such that its outer diameter is only slightly larger than the outer diameter of the pull wire. In some embodiments, the outer dimensions of the securing element diameter are small in comparison to the anchoring element dimensions, thereby minimizing any increase in the overall circumferential profile of the medical instrument. In some embodiments, the securing element may be plated with particular compounds or elements to enhance solderability and/or to assist in maintaining a low solder profile.

In other embodiments, the pull wire may run within a channel of the instrument body, and a proximal surface of the securing element may be positioned adjacent to a distal surface of the instrument body such that the external circumference of the instrument remains unchanged. In some embodiments, a proximal surface of the securing element may be soldered to a distal surface of the instrument body such that the external circumference of the instrument remains unchanged. For example, a proximal surface of the crimp may be soldered on a distal surface of the instrument body. In such embodiments, the system maintains an overall low circumferential profile because the securing element is coupled to the instrument so that the (cross-sectional) outer perimeter of the securing element does not extend past the (cross-sectional) outer perimeter of the instrument. In some embodiments, the securing element may be held circumferentially in position against the instrument by a securing ring comprised of hard plastic, metal, and/or other materials known in the art.

According to various embodiments, medical procedures, such as biopsy procedures, may be performed using a teleoperational system to guide instrument delivery. Those of skill in the art will realize that the devices, systems, and methods described herein may be utilized in similar (e.g., non-teleoperational) applications benefiting from more effective attachment of pull wires to medical instruments.

Referring to FIG. 1 of the drawings, a teleoperational medical system for use in, for example, medical procedures including diagnostic, therapeutic, or surgical procedures, is generally indicated by the reference numeral 100. As will be described, the teleoperational medical systems of this disclosure are under the teleoperational control of a surgeon. In alternative embodiments, a teleoperational medical system may be under the partial control of a computer programmed to perform the procedure or sub-procedure. In still other alternative embodiments, a fully automated medical system, under the full control of a computer programmed to perform the procedure or sub-procedure, may be used to perform procedures or sub-procedures. As shown in FIG. 1, the teleoperational medical system 100 generally includes a teleoperational assembly 102 mounted to or near an operating table O on which a patient P is positioned. A medical instrument system 104 is operably coupled to the teleoperational assembly 102. An operator input system 106 allows a surgeon or other type of clinician S to view images of or representing the surgical site and to control the operation of the medical instrument system 104. The operator input system 106 may be referred to as a master or surgeon's console.

The operator input system 106 may be located at a surgeon's console, which is usually located in the same room as operating table O. It should be understood, however, that the surgeon S can be located in a different room or a completely different building from the patient P. Operator input system 106 generally includes one or more control device(s) for controlling the medical instrument system 104. More specifically, in response to the surgeon's input commands, the control system 112 effects servomechanical movement of medical instrument system 104. The control device(s) may include one or more of any number of a variety of input devices, such as hand grips, joysticks, trackballs, data gloves, trigger-guns, hand-operated controllers, voice recognition devices, touch screens, body motion or presence sensors, and the like. In some embodiments, the control device(s) will be provided with the same degrees of freedom as the medical instruments of the teleoperational assembly to provide the surgeon with telepresence, the perception that the control device(s) are integral with the instruments so that the surgeon has a strong sense of directly controlling instruments as if present at the surgical site. In other embodiments, the control device(s) may have more or fewer degrees of freedom than the associated medical instruments and still provide the surgeon with telepresence. In some embodiments, the control device(s) are manual input devices which move with six degrees of freedom, and which may also include an actuatable handle for actuating instruments (for example, for closing grasping jaws, applying an electrical potential to an electrode, delivering a medicinal treatment, and the like).

The teleoperational assembly 102 supports the medical instrument system 104 and may include a kinematic structure of one or more non-servo controlled links (e.g., one or more links that may be manually positioned and locked in place, generally referred to as a set-up structure) and a teleoperational manipulator. The teleoperational assembly 102 includes plurality of motors that drive inputs on the medical instrument system 104. These motors move in response to commands from the control system (e.g., control system 112). The motors include drive systems which when coupled to the medical instrument system 104 may advance the medical instrument into a naturally or surgically created anatomical orifice. Other motorized drive systems may move the distal end of the medical instrument in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the motors can be used to actuate an articulable end effector of the instrument for grasping tissue in the jaws of a biopsy device or the like.

The teleoperational medical system 100 also includes an image capture system 108 with one or more sub-systems for capturing images from the surgical workspace at the distal end of the medical instrument system 104. The system operator sees images, captured by an image capture system 108, presented for viewing on a display system 110 operatively coupled to or incorporated into the operator input system 106. The display system 110 displays an image or representation of the surgical site and medical instrument system(s) 104 as generated by sub-systems of the image capture system 108. The display system 110 and the operator input system 106 may be oriented so the operator can control the medical instrument system 104 and the operator input system 106 with the perception of telepresence. The display system 110 may include multiple displays such as separate right and left displays for presenting separate images to each eye of the operator, thus allowing the operator to view stereo images.

In some embodiments, as shown in FIG. 1, the teleoperational medical system 100 may also include a variety of other delivery/auxiliary systems 109. The delivery/auxiliary systems may be drug delivery systems, fluid delivery systems, or other auxiliary systems known in the art.

Alternatively or additionally, the display system 110 may present images of the surgical site (and/or anatomical site) recorded and/or imaged preoperatively or intra-operatively using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, and the like. The presented preoperative or intra-operative images may include two-dimensional, three-dimensional, or four-dimensional (including e.g., time based or velocity based information) images and associated image data sets for reproducing the images.

The teleoperational medical system 100 also includes a control system 112. The control system 112 includes at least one memory and at least one processor (not shown), and typically a plurality of processors, for effecting control between the medical instrument system 104, the operator input system 106, the image capture system 108, and the display system 110. The control system 112 also includes programmed instructions (e.g., a computer-readable medium storing the instructions) to implement some or all of the methods described in accordance with aspects disclosed herein. While control system 112 is shown as a single block in the simplified schematic of FIG. 1, the system may include two or more data processing circuits with one portion of the processing optionally being performed on or adjacent the teleoperational assembly 102, another portion of the processing being performed at the operator input system 106, and the like. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, control system 112 supports wireless communication protocols such as Bluetooth, IrDA, HomeRF, IEEE 802.11. DECT, and Wireless Telemetry.

In some embodiments, the control system 112 may include one or more servo controllers that receive force and/or torque feedback from the medical instrument system 104. Responsive to the feedback, the servo controllers transmit signals to the operator input system 106. The servo controller(s) may also transmit signals instructing teleoperational assembly 102 to move the medical instrument system(s) 104 which extend into an internal surgical site within the patient body via openings in the body. Any suitable conventional or specialized servo controller may be used. A servo controller may be separate from, or integrated with, teleoperational assembly 102. In some embodiments, the servo controller and teleoperational assembly are provided as part of a teleoperational arm cart positioned adjacent to the patient's body.

The teleoperational medical system 100 may further include optional operation and support systems (not shown) such as illumination systems, steering control systems, irrigation systems, and/or suction systems. In alternative embodiments, the teleoperational system may include more than one teleoperational assembly and/or more than one operator input system. The exact number of manipulator assemblies will depend on the surgical procedure and the space constraints within the operating room, among other factors. The operator input systems may be collocated, or they may be positioned in separate locations. Multiple operator input systems allow more than one operator to control one or more manipulator assemblies in various combinations.

Figure 2:
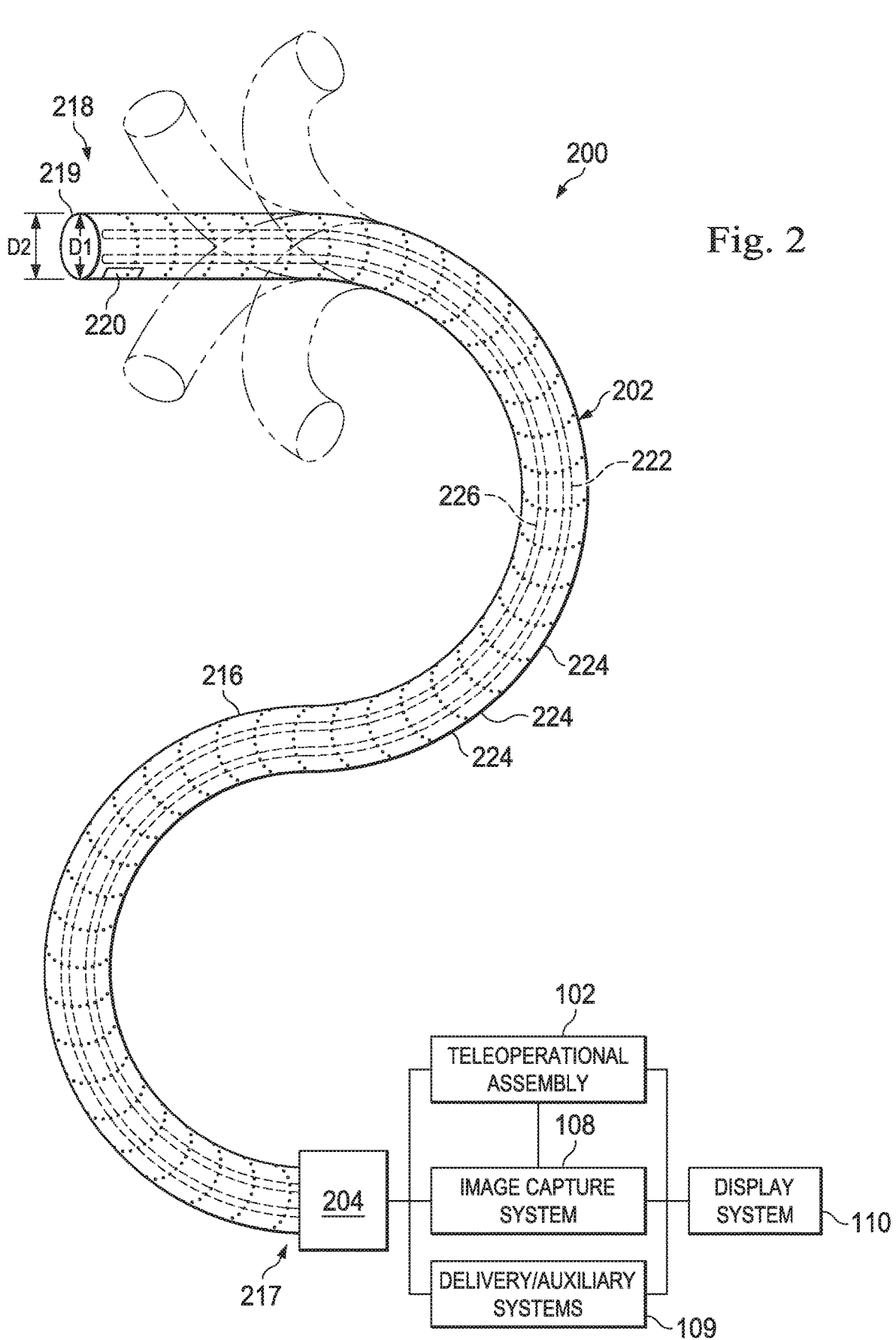
FIG. 2 is a diagram showing an illustrative medical instrument system comprising an endoscopic visualization system according to one embodiment of the present disclosure.

FIG. 2 illustrates a medical instrument system 200, which may be used as the medical instrument system 104 of teleoperational medical system 100 for insertion into a patient's body at either a natural orifice or a surgically created orifice. Alternatively, the medical instrument system 200 may be used for non-teleoperational exploratory procedures or in procedures involving traditional manually operated medical instruments, such as endoscopy.

The instrument system 200 includes a catheter system 202 coupled to an instrument body housing 204. The catheter system 202 includes an elongated flexible catheter body 216 having a proximal end 217 and a distal end or tip portion 218. The flexible body 216 has a working channel 219 with an inner diameter D1 and an outer diameter D2. The working channel or tool channel 219 may be sized to receive an instrument or tool and/or to direct fluid through the flexible body. In one embodiment, the flexible body 216 has an outer diameter D2 of approximately 3.2 mm. In one embodiment, the flexible body 216 has an approximately 2 mm inner diameter (i.e., the working channel 219 has an inner diameter D1 of approximately 2 mm). Other inner and outer diameters are contemplated, including both larger and smaller diameters. The entire length of the body 216, between the distal end 218 and the proximal end 217, may be effectively divided into the segments 224.

The medical instrument system may optionally include a position sensor system 220. The position sensor system 220 may be a component of an EM sensor system with the sensor 220 including one or more conductive coils that may be subjected to an externally generated electromagnetic field. The catheter system 202 may optionally include a shape sensor 222 for determining the position, orientation, speed, velocity, pose, and/or shape of the catheter tip at distal end 218 and/or of one or more segments 224 along the body 216. The shape sensor 222 may include an optical fiber aligned with the flexible catheter body 216 (e.g., provided within an interior channel (not shown) or mounted externally). In one embodiment, the optical fiber has a diameter of approximately 200 μm. In other embodiments, the dimensions may be larger or smaller. The optical fiber of the shape sensor system 222 forms a fiber optic bend sensor for determining the shape of the catheter system 202.

The flexible catheter body 216 includes one or more working channels sized and shaped to receive an auxiliary instrument 226 (not shown). For example, in some embodiments, the auxiliary instrument 226 may be received within the working channel 219. Auxiliary instruments may include, for example, image capture probes, biopsy instruments, laser ablation fibers, or other surgical, diagnostic, or therapeutic tools. Auxiliary tools may include end effectors having a single working member such as a scalpel, a blunt blade, an optical fiber, or an electrode. Other end effectors may include, for example, forceps, graspers, scissors, or clip appliers. Examples of electrically activated end effectors include electrosurgical electrodes, transducers, sensors, and the like.

The auxiliary instrument 226 may house cables, linkages, or other actuation controls (not shown) that extend between the proximal and distal ends of the instrument to controllably bend the distal end of the instrument. Steerable instruments are described in detail in U.S. Pat. No. 7,316,681 (filed on Oct. 4, 2005) (disclosing "Articulated Surgical Instrument for Performing Minimally Invasive Surgery with Enhanced Dexterity and Sensitivity") and U.S. patent application Ser. No. 12/286,644 (filed Sep. 30, 2008) (disclosing "Passive Preload and Capstan Drive for Surgical Instruments"), which are incorporated by reference herein in their entireties.

The flexible catheter body 216 may also house cables, linkages, or other steering controls (not shown) that extend between the housing 204 and the distal end 218 to controllably bend the distal end 218 as shown, for example, by the broken dashed line depictions of the distal end. Steerable catheters are described in detail in U.S. patent application Ser. No. 13/274,208 (filed Oct. 14, 2011) (disclosing "Catheter with Removable Vision Probe"), which is incorporated by reference herein in its entirety. In embodiments in which the instrument system 200 is actuated by a teleoperational assembly, the housing 204 may include drive inputs that removably couple to and receive power from motorized drive elements of the teleoperational assembly. In embodiments in which the instrument system 200 is manually operated, the housing 204 may include gripping features, manual actuators, or other components for manually controlling the motion of the instrument system. The catheter system may be steerable or, alternatively, the system may be non-steerable with no integrated mechanism for operator control of the instrument bending. Also or alternatively, one or more lumens, through which medical instruments can be deployed and used at a target surgical location, are defined in the walls of the flexible body 216.

In various embodiments, the medical instrument system 200 may include a flexible bronchial instrument, such as a bronchoscope or bronchial catheter, for use in examination, diagnosis, biopsy, or treatment of a lung. The system 200 is also suited for navigation and treatment of other tissues, via natural or surgically created connected passageways, in any of a variety of anatomical systems, including the colon, the intestines, the kidneys, the brain, the heart, the circulatory system, and the like. In various embodiments, the medical instrument may include a rigid cannula (e.g. a rigid endoscope) rather than a flexible catheter. In the embodiment of FIG. 2, the medical instrument system 200 is teleoperated within the teleoperational medical system 100. In an alternative embodiment, the teleoperational assembly 102 may be replaced by direct operator control. In the direct operation alternative, various handles and operator interfaces may be included for hand-held operation of the instrument.

To operate effectively, cables (or pull wires), linkages, or other elongate steering or actuation elements may extend between the instrument body housing 204 and the distal end 218. In some embodiments, the steering devices may include distal portions attached to the distal end 218 and proximal portions attached within the instrument body housing 204. One known method for pull wire attachment involves directly soldering a solid pull wire to a portion of the distal end 218 of the flexible catheter body 216. As mentioned above, this method of attachment for solid pull wires presents various problems, such as weakening of the pull wire at the connection point and decreased safety due to the high bending stiffness of the solid pull wires. Cable metal wires or braided pull wires may be desirable over solid metal pull wires because of their decreased bending stiffness. In particular, tungsten cable wires are desirable because of their high tensile strength and high modulus, which allows for quicker responses when the pull wires are actuated. However, cable metal wires such as tungsten cable wires have proved difficult to attach to medical instruments 200 without increasing the overall circumference or profile of the instrument at the attachment site. For example, tungsten cable wires have traditionally been attached to the instrument using a mechanical attachment feature on the distal end of the instrument that engages a crimp surrounding the distal end of the wire (e.g., the mechanical attachment feature locks the crimp when the wire is actuated). This often necessitates a larger circumference or profile of the instrument at the attachment site. In accordance with the present disclosure, the pull wire assemblies and pull wire attachment systems described herein allows for increased safety, decreased bending stiffness of the pull wire, and an overall lower circumferential profile of the medical instrument at the attachment site (e.g., the distal end 218 of the flexible catheter body 216 shown in FIG. 2).

Figures 3, 4:
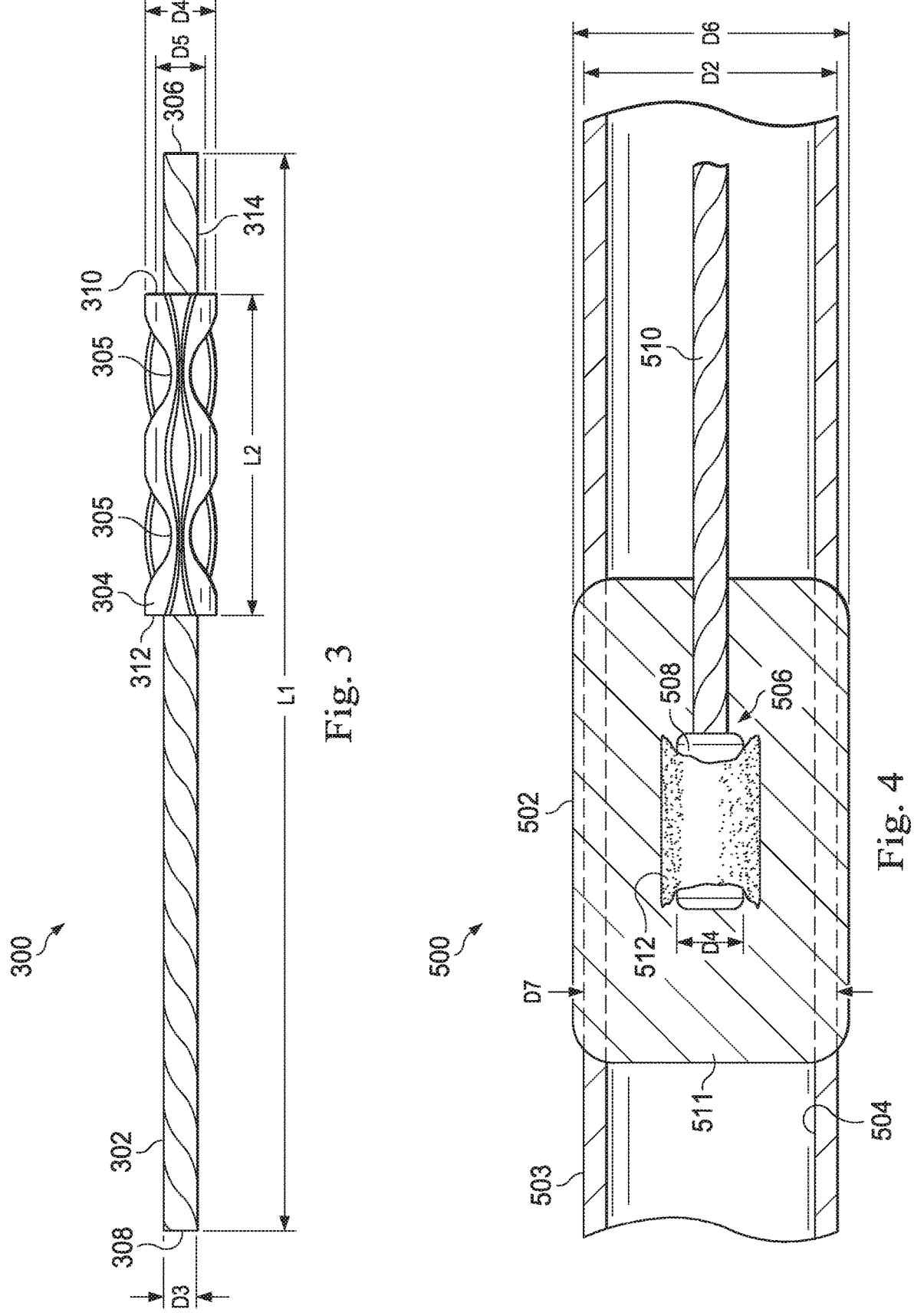
FIG. 3 is a side view of an exemplary pull wire assembly including a securing element positioned around a pull wire.
FIG. 4 is a side view of an exemplary pull wire attachment system coupling an exemplary pull wire assembly to an exemplary anchoring element of an exemplary medical device according to one embodiment of the present disclosure.

FIG. 3 is a side view of an exemplary pull wire assembly 300 including a pull wire 302 and a securing element 304. The pull wire 302 comprises any suitable elongate control device, including an actuation or control cable, tendon, solid wire, or braided wire. The pull wire 302 includes a distal end 306 and a proximal end 308 and a length L1 extending therebetween. In some embodiments, the length L1 of the pull wire 302 extends from the distal end 218 of the flexible catheter body 216 to the proximal end 217. However, the length L1 may be shorter or longer in other embodiments. For example, in some embodiments, the pull wire 302 may be shorter and terminate along the flexible catheter body 216 at a position proximal to the distal end 218. In other embodiments, the pull wire 302 may be longer and wound or otherwise bent to attach to the proximal end 217. In the pictured embodiment, the pull wire 302 comprises a cylindrical structure having an outer diameter D3. The length L1 may range from 700 mm to 1000 mm. The outer diameter D3 may range from 0.15 mm to 0.25 mm. These dimensions are presented for exemplary purposes only, and other dimensions are contemplated.

In the pictured embodiment, the securing element 304 is shaped and configured as a crimp that is coupled to a portion of the pull wire 302 with crimped portions 305. In the pictured embodiment, the securing element 304 has a closed, cylindrical, tubular form. In other embodiments, the securing element 304 may have any of a variety of other shapes or forms such as, by way of non-limiting example, rectangular, cuboid, polygonal, semi-circular, or open cylinder. The securing element 304 extends from a securing element distal end 310 to a securing element proximal end 312. In the depicted embodiment, the securing element 304 comprises a hollow, cylindrical tube having a length L2, an outer diameter D4, and an inner luminal diameter D5 (shown in FIG. 5). In the pictured embodiment, the length L1 of the pull wire 302 exceeds the length L2 of the securing element 304. In some embodiments, the outer diameter D4 of the securing element 304 only slightly exceeds the outer diameter D3 of the pull wire 302 such that the securing element 304 does not greatly increase the profile of the pull wire 302. The length L2 may range from 5 mm to 10 mm. The outer diameter D4 may range from 0.2 mm to 0.3 mm. The inner diameter D5 may range from 0.2 mm to 0.3 mm. In some embodiments, the inner luminal diameter D5 of the securing element 304 only slightly exceeds (e.g., by about 0.04-0.08 mm) the outer diameter D3 of the pull wire 302 such that the securing element 304 may have a frictional fit with the pull wire 302 (e.g., to retain a sufficient gripping force on the pull wire 302). These dimensions are presented for exemplary purposes only, and other dimensions are contemplated.

In exemplary embodiments, the securing element 304 is permanently secured (e.g., compressed or adhesively affixed) around the pull wire 302 such that the inner diameter D5 becomes substantially the same as the outer diameter D3 of the pull wire 302. In the pictured embodiment, an inner cylindrical face 309 (not shown) of the securing element 304 extends circumferentially 360 degrees around the pull wire 302 such that the securing element 304 exerts a substantial gripping force on the pull wire 302. In other embodiments, the securing element 304 may comprise an open structure that extends less than 360 degrees around the pull wire 302. The length L2 may be relatively shorter or longer than indicated by the pictured embodiment in FIG. 3 provided that the length L2 is sufficiently long such that the securing element 304 maintains gripping force on the pull wire 302.

In some embodiments, the securing element 304 is compressed around the pull wire 302 near the distal end 306 of the pull wire 302 such that the distal end 306 of the pull wire 302 and the distal end 310 of the securing element 304 are substantially co-planar. However, in other embodiments, including the pictured embodiment, the securing element 304 may be compressed around a portion of the pull wire 302 at a location between the distal end 306 and the proximal end 308. In such embodiments, a distal portion 314 of the pull wire 302 may be mechanically detached from the pull wire 302 at a location substantially co-planar with the distal end 310 of the securing element 304. In various embodiments, the distal portion 314 may be mechanically detached by cutting, sawing, slicing, or other forms of severing. Optionally, solder may be applied to secure the generally co-planar ends of the securing element and pull wire. The solder may add approximately 0.04-0.08 mm to the length of the construction. In another embodiment, the a lumen extends only through a partial length of the securing element. In this embodiment, the securing element caps the distal end 306 of the pull wire 302 such that a distal portion of the securing element extends distally of the distal end 306 of the pull wire.

In the pictured embodiment, the pull wire 302 comprises a cable metal wire. In other embodiments, the pull wire may be a solid wire or another type of braided wire. In some embodiments, the pull wire 302 is comprised of tungsten. In other embodiments, the pull wire 302 may be comprised of other polymers or metals, including without limitation, stainless steel, copper, tin, or other metals. Similarly, the securing element 304 may be formed of any of a variety of suitable polymers or metals. In some embodiments, the securing element 304 is comprised of stainless steel. In other embodiments, the securing element 304 may be comprised of aluminum, copper, gold, tin, or other solderable metals. In some embodiments, the securing element 304 is Ni/Au plated to enhance the solderability while maintaining a low solder profile.

FIG. 4a illustrates a side view of an exemplary pull wire attachment system 500 according to one embodiment of the present disclosure. The pull wire attachment system 500 comprises an exemplary pull wire assembly 506 coupled to an exemplary anchoring element 502. The anchoring element 502 is shown positioned on an exemplary medical instrument 503, which includes a working channel 504. The working channel 504 may be substantially similar to the working channel 219 of the catheter system 202 shown in FIG. 2. The pull wire assembly 506 comprises a securing element 508 and a pull wire 510. The pull wire assembly 506 may be substantially identical to the pull wire assembly 300 described above in relation to FIGS. 3 and 4. The securing element 508 and the pull wire 510 may be the same as the securing element 304 and the pull wire 302, respectively, shown in FIGS. 3 and 4.

In some embodiments, the anchoring element 502 is fixedly secured to the medical instrument 503. In some embodiments, the anchoring element 502 may be fixedly attached to the medical instrument 503 via mechanical locking mechanisms, welding, compression, or other methods known in the art. In the pictured embodiment, the anchoring element 502 comprises a cylindrical tube or sleeve that circumferentially surrounds the medical instrument 503. In other embodiments, the anchoring element 502 may comprise a disc, annular ring, or plate-like structure positioned about the medical instrument 503 or extending through the medical instrument 503. In some embodiments, the anchoring element 502 is formed of stainless steel or a polymer compound. In other embodiments, the anchoring element 502 may be comprised of aluminum, copper, gold, tin, tungsten, or other solder-able metals known in the art. The medical instrument 503 includes an outer diameter D2. The anchoring element 502 includes an outer diameter D6 and an inner luminal diameter D7. The outer diameter D2 of the instrument may range from 2.5 mm to 3.5 mm. The outer diameter D6 of the anchoring element may exceed the diameter of outer diameter D2 of the instrument by less than approximately 0.1 mm. These dimensions are presented for exemplary purposes only, and other dimensions are contemplated. In the pictured embodiment, the inner diameter D7 of the anchoring element 502 is sized to be only slight larger than the outer diameter D2 of the medical instrument 503 to provide a close fit. In the pictured embodiment, the outer diameter D6 of the anchoring element 502 is only slightly larger than the outer diameter D2 of the medical instrument 503.

In the pictured embodiment, the pull wire assembly 506 is fixedly attached to an outer surface 511 of the anchoring element 502. The coupling of the pull wire assembly 506 to the anchoring element 502 anchors the distal end of the pull wire 510 and prevents the proximal translation of the distal end of the pull wire 510 along a longitudinal axis of the medical instrument 503 past the anchoring element 502. In the pictured embodiment, the pull wire assembly 506 is attached to the anchoring element 502 by soldering the pull wire assembly 506 (i.e., the securing element 508) to the outer surface 511 of the anchoring element 502 using solder 512. In one embodiment, the securing element 508 is attached to the anchoring element 502 using 80/20 AuSn solder, which has a high tensile strength and a melting temperature of 280 degrees Celsius. In the pictured embodiment, the outer diameter D4 of the securing element 508 is substantially smaller than the outer diameter D6 of the anchoring element 502 such that the overall pull wire attachment system 500 maintains a relatively low circumferential profile even after soldering. The outer diameter D4 of the securing element 508 is substantially small compared to the outer diameter D6 of the anchoring element 502, allowing the soldered combination of the securing element 508, the solder 512, and the anchoring element 502 to only slightly increase the overall cross-sectional profile of the medical instrument 503 and to keep profile lower than traditional mechanical lock attachment methods for cable pull wires. In the pictured embodiment, the overall circumferential profile is only slightly larger than the outer diameter D2 of the medical instrument 503.

In some embodiments, an active flux, such as zinc chloride, ammonia chloride, carboxylic acids, or other fluxes known in the art, may be used to enhance the wettability of the solder to both the securing element 508 and the anchoring element 502. In still other embodiments, as mentioned above, the securing element 508 may be Ni/Au plated to enhance the solderability while maintaining a low solder profile. In other embodiments, the pull wire attachment system 506 may be attached to the outer surface 511 of the anchoring element 502 by laser welding.

Figures 5, 6:
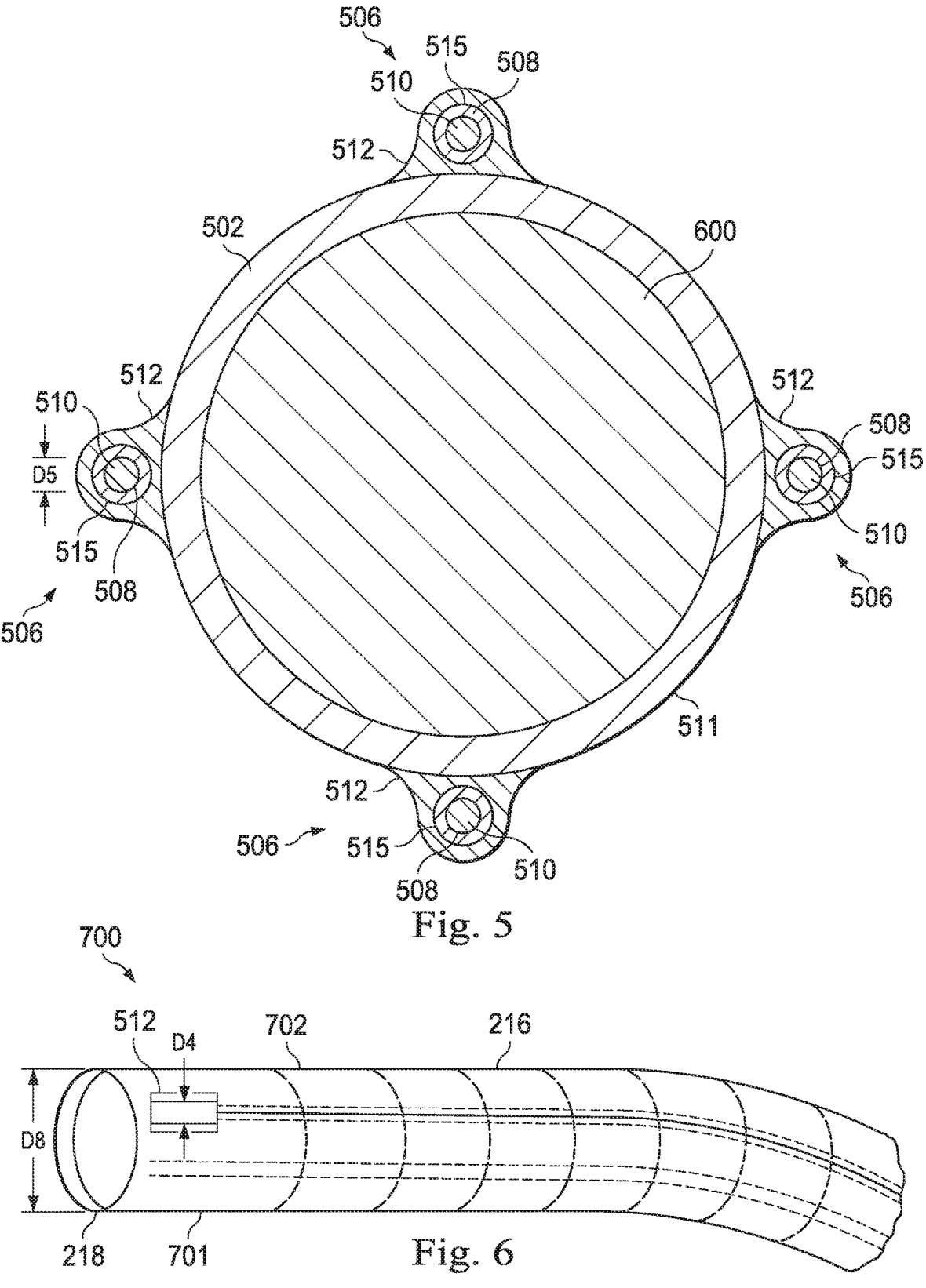
FIG. 5 is a cross-sectional view of a distal portion of an exemplary medical device including multiple exemplary pull wire attachment systems according to one embodiment of the present disclosure.
FIG. 6 is a perspective view of an exemplary pull wire attachment system according to one embodiment of the present disclosure.

FIG. 5 is a cross-sectional view of an exemplary medical instrument 600 including multiple pull wires 510 attached by multiple pull wire attachment systems 500 such as that shown in FIG. 4. In the pictured embodiment, the anchoring element 502 comprises a cylindrical sleeve positioned around the instrument 600. A plurality of pull wire assemblies 506, comprising the securing elements 508 and the pull wires 510, are attached around the circumference of the anchoring element 502. In the pictured embodiment, the medical instrument 600 includes four pull wire assemblies 506 attached at approximately 90 degree intervals around the circumference of the anchoring element 502. In particular, the pull wire assemblies 506 are secured by soldering with the solder 512 an outer surface 515 of the securing element 508 to the outer surface 511 of the anchoring element 502.

In other embodiments, the assemblies 506 may be laser welded to the anchoring element 502. Various embodiments may include any number and arrangement of pull wire assemblies 506 attached to the anchoring element 502. For example, other embodiments may have more or less more pull wire assemblies 506 secured to the anchoring element 502. In other embodiments, the pull wire assemblies 506 may be positioned about the anchoring element 502 at intervals of varying degrees. For example, an exemplary embodiment may have 6 pull wire assemblies 506 secured to the anchoring element 502 at 60 degree intervals around the circumference of the anchoring element 502.

In other embodiments, the pull wire assembly 506 may be directly attached to an external surface of the medical instrument, without an intervening anchor element (e.g., the anchor element 502). FIG. 6 is a perspective view of an embodiment of an exemplary pull wire attachment system 700 where the pull wire assembly 600 is attached directly to the distal end 218 of the flexible catheter body 216 (shown in FIG. 2). In some embodiments, the distal end 218 of the flexible catheter body 216 may include a distal tip 701 comprised of metal, such as stainless steel or other solderable metals known in the art. As depicted in FIG. 5, the securing element 508 may be attached to an external surface 702 (e.g., by the solder 512) of the distal tip 701. In such embodiments, the distal tip 701 effectively performs the function of the anchoring element 502 described above. In exemplary embodiments, the overall diameter of the securing element 508 and the solder 512 is sized such that the resulting soldered combination of the securing element 508 to the metal distal tip 701 maintains a relatively low cross-sectional profile. To maintain the low overall profile, the diameter D4 of the securing element 508 may be substantially smaller than an outer diameter D8 of the distal tip 701. The outer diameter D8 may range from 3.0 mm to 3.5 mm. These dimensions are presented for exemplary purposes only, and other dimensions are contemplated. In other embodiments, the securing element 508 may be attached by laser welding to the metal distal tip 701.

Figure 7A:
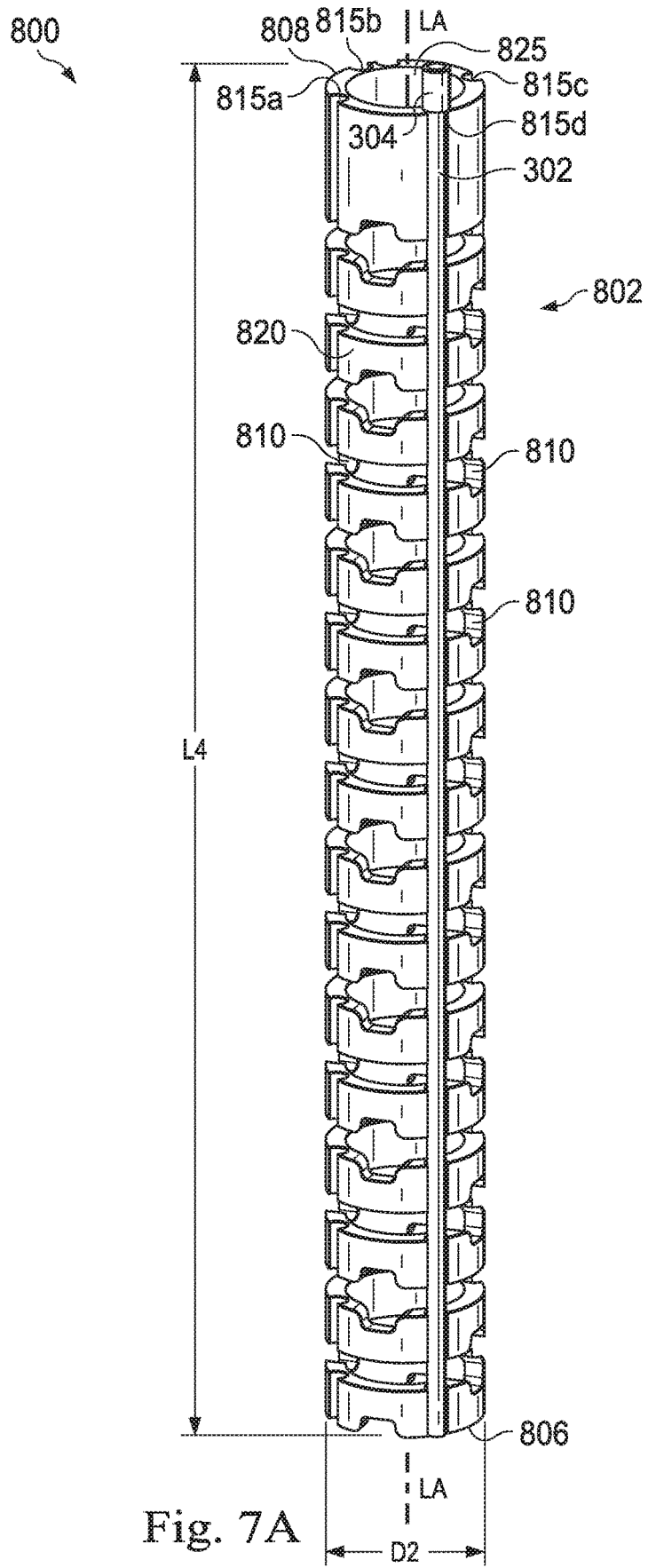
FIG. 7A is a perspective view of a distal portion of an exemplary medical device according to one embodiment of the present disclosure.

FIG. 7A illustrates a perspective view of an exemplary medical instrument 800 including a steerable tube 802 and a single pull wire assembly 300 (as shown in FIG. 3). In some embodiments, the steerable tube 802 may be the same as the distal end 218 of the flexible catheter body 216 described above with reference to FIG. 2. In the embodiment pictured in FIG. 6, the steerable tube 802 comprises a hollow, elongate, tubular member having a length L4 extending from a proximal end 806 to a distal end 808. In the pictured embodiment, the steerable tube 802 has a cylindrical shape in the non-flexed state and extends along a longitudinal axis LA.

The steerable tube 802 may be made of any suitable biocompatible material that provides the requisite tensile and flexural properties. Suitable materials may include, by way of non-limiting example, shape memory material such as Nitinol, stainless steel, and plastics. In some embodiments, the steerable tube 802 is made from the same material throughout (e.g., Nitinol from the proximal end 806 to the distal end 808). In other embodiments, the steerable tube 802 may be made from two or more different materials (e.g., stainless steel in a less flexible zone and Nitinol in a more flexible zone).

In the pictured embodiment, the steerable tube 802 includes a plurality of cuts or cut-out features 810. The cut-out features 810 are formed with a pattern that provides an optimal balance of axial, bending, and torsional stiffness. In the pictured embodiment, the cut-out features are formed substantially perpendicular to the longitudinal axis LA. The cut-out features 810 allow the steerable tube 802 to bend in multiple dimensions. In some embodiments, the frequency and pattern of cuts in any given portion of the steerable tube 802 may determine the flexibility of that portion. In some embodiments, a higher spatial frequency of cuts may correspond to a higher flexibility. In the pictured embodiment, the cut-out features 810 only extend along a portion of the steerable tube 802. In other embodiments, the cut-out features may extend the entire length of the steerable tube 802, or along a different portion of the steerable tube 802. The cut-out features 810 illustrated in the drawings are merely exemplary, and are not intended to be limiting in number, type, arrangement, or shape. In various embodiments, the steerable tube 802 may have any number, type, shape, and arrangement of cut-out features 810.

In the pictured embodiment, the steerable tube 802 includes channels or grooves 815a-d configured to receive the pull wires 302. The channels 815a-e may comprise indentations, grooves, or enclosed passageways. In the pictured embodiment, the steerable tube 802 includes four grooves 815a, 815b, 815c, and 815d that are configured to carry four individual pull wires 302. In the pictured embodiment, the grooves 815a-d have a generally hemispherical cross-sectional shape. In other embodiments, the grooves 815a-d may have any of a variety of cross-sectional shapes, including, by way of non-limiting example, a complete or closed circle, an incomplete or partial circle, an incomplete or partial polygon, or a complete or closed polygon. In some embodiments, the grooves 815a-d may have an open cross-sectional shape. In other embodiments, the grooves 815a-d may have a closed cross-sectional shape.

The grooves 815a, 815b, 815c, and 815d are disposed circumferentially around the steerable tube 802 on an outer surface 820 of the steerable tube 802. The circumferential position of the grooves 815a-d on the steerable tube 802 may correlate with the circumferential position of the pull wires 302 along the medical instrument 800, and are generally parallel to the longitudinal axis LA of the steerable tube 802. Thus, the pull wires 302 may be slidably received within the grooves 815 of the steerable tube 802 without terminating or kinking the pull wires 302. This configuration allows for the pull wires 302 to extend alongside the steerable tube 802 while maximizing the potential inner diameter D1 (shown in FIG. 7B) of a lumen 825 of the steerable tube 802, minimizing the outer diameter D2 of the steerable tube 802, and maximizing a wall thickness T1 (shown in FIG. 7B) of the steerable tube 802.

Figure 7B:
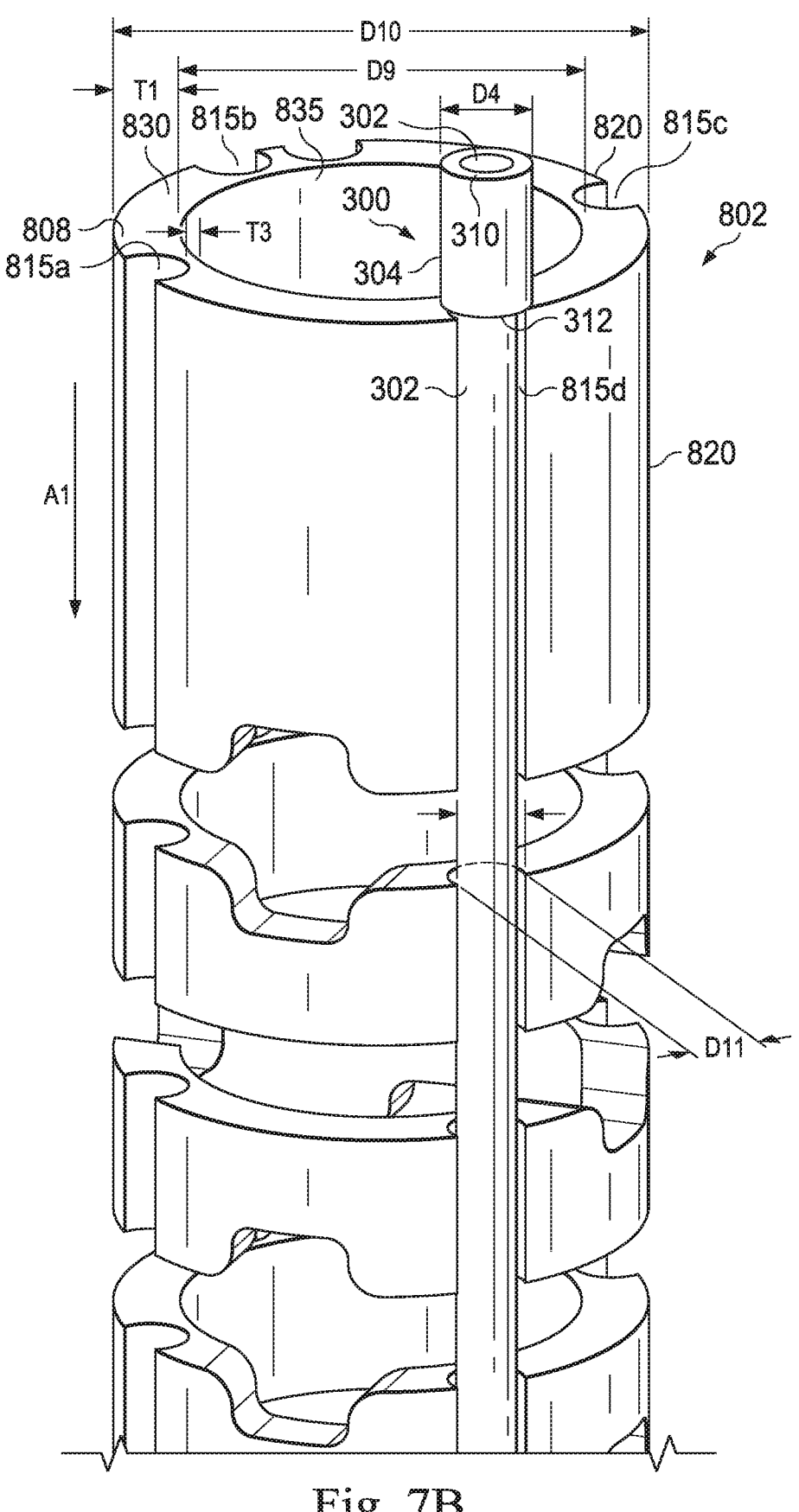
FIG. 7B is a more detailed perspective view of the distal portion of the exemplary medical device shown in FIG. 7A, including an exemplary pull wire attachment system according to one embodiment of the present disclosure.

FIG. 7B is a more detailed perspective view of the steerable tube 802 shown in FIG. 7A. As shown in FIG. 7B, the steerable tube 802 has a wall 830 and a wall thickness T1 extending between an inner surface 835 and the outer surface 820 of the wall 830. The tube 802 has an inner diameter D9 that spans the lumen 825, and an outer diameter D10 that spans the tube 802. The inner diameter D9 may range from 1.5 to 2.5 mm, and the outer diameter D10 may range from 2.5 to 3.5 mm. These measurements are provided for exemplary purposes only, and are not intended to be limiting. The wall thickness T1 of the steerable tube 802 may be substantially uniform in the areas without the grooves 815, and the wall thickness T1 may decrease by a substantially uniform amount in the area of the grooves 815. The steerable tube 802 may have a substantially uniform wall thickness T3 in the area of the grooves 815. The wall thickness T3 is less than the wall thickness T1. In some embodiments, the thickness T1 will range from 0.25 to 0.38 mm. In some embodiments, the thickness T3 will range from 0.07 to 0.127 mm. These measurements are presented for exemplary purposes only, and are not intended to be limiting. Other wall thicknesses are contemplated.

FIG. 7B more clearly illustrates the pull wire assembly 300, including the pull wire 302 and the securing element 304, in relation to the steerable tube 802. Although an individual pull wire 302 may be disposed within each the grooves 815, for the sake of simplicity, only one pull wire 302 is shown in relation to the groove 815d. In some embodiments, the pull wire 302 may be secured within the groove 815d by plastic lamination or a flexible sheath (not shown) surrounding the entire steerable tube 802.

In the pictured embodiment, the pull wire assembly 300 is movably coupled to the steerable tube 802 in a manner that allows the pull wire 302 to axially translate within the groove 815d but prevents the pull wire 302 from moving too far in the proximal direction depicted by arrow A1. In particular, the pull wire 302 is disposed within the groove 815d and runs parallel to the longitudinal axis LA of the steerable tube 802. The pull wire assembly 300, including the securing element 304 coupled to a distal end of the pull wire 302, is positioned distal to the distal end 808 of the steerable tube 802. In the pictured embodiment, the outer diameter D4 of the securing element 304 (as shown in FIG. 3) is sized to be only slightly larger than the wall thickness T1 of the steerable tube 802, thereby affixing the pull wire assembly to the instrument 800 without substantially increasing the overall circumferential profile of the instrument 800 at the steerable tube 802.

As shown in FIGS. 7B, the securing element 304 extends from the securing element proximal end 312 to the securing element distal end 310. In the pictured embodiment, the securing element 304 is positioned distal to the steerable tube 802 such that, with articulation of the tube 802 and actuation of the pull wire 302, the proximal end 312 of the securing element 304 contacts the distal end 808 of the steerable tube 802 to halt the proximal translation of the pull wire 302. The securing element 304 is sized and positioned relative to the groove 815d such that articulation of the pull wire 302 does not cause the securing element 304 to slide proximally into the groove 815d. In particular, the outer diameter D4 of the securing element 304 is sized to be greater than the inner diameter D11 of the groove 815d. Thus, the proximal end 312 of the securing element 304 is caught upon the distal end 808 of the steerable tube and cannot enter the groove 815d because the groove 815d is too small to allow passage of the securing element 304. In such an embodiment, the steerable tube 802 acts as the anchoring element to prevent the proximal translation of the distal end of the pull wire 302 (proximally) past the steerable tube 802.

In some embodiments, the proximal end 312 of the securing element 304 is permanently affixed to the distal end 808 of the steerable tube 802 such that the pull wire assembly 300 is fixedly attached to the distal end 808 of the steerable tube 802. In various embodiments, the proximal end 312 of the securing element 304 may be permanently affixed to the distal end 808 of the steerable tube 802 via soldering or by laser welding. In such embodiments, the solder may be 80/20 Au/Sn or other solderable materials. In other embodiments, the securing element 304 may be held circumferentially at the distal end 808 of the steerable tube 802 by a securing ring (not shown). In some embodiments, the securing ring may be comprised of a stiff plastic, such as Nylon 12. In other embodiments, the securing ring may be formed of stainless steel, tin, aluminum, or another metal.

In various alternative embodiments similar to FIG. 7B, the securing element 304 may be omitted and the pull wire 302 may be soldered directly to the distal end 808 of the steerable tube 802 if the distal end is formed of a suitable material such as stainless steel. In this or other embodiments, a polymer covering (e.g., a clear plastic sleeve) may cover the solder and the distal end of the steerable tube to provide a smooth surface.

The devices, systems, and methods of this disclosure may be used for anchoring or attaching actuation or control elements (e.g., cables or pull wires) to a medical instrument, such as a catheter. In particular, a securing element (e.g., a crimp) is coupled to the elongate control element (e.g., a pull wire) to form a pull wire assembly and the securing element is then attached to an anchoring element located on a steerable portion of the instrument body. In one embodiment, the pull wire assembly is attached to the instrument via soldering of the securing element to the anchoring element. In other embodiments, the securing element is soldered directly to a metal portion of the instrument body. In general, the cross-sectional dimensions of the securing element are small compared to the dimensions of the instrument body to ensure that the overall circumferential profile of the system remains low, which is desirable in invasive medical procedures to minimize trauma to patient tissues. In some embodiments, a distal portion of the instrument includes a steerable tube that includes channels or grooves that are configured to receive the actuation elements (e.g. pull wires). In such embodiments, the securing element of the pull wire assembly is positioned distal to the distal end of the steerable tube, and may act to limit the axial translation of the pull wire in the proximal direction. In such embodiments, the outer diameter of the securing element is less than or equal to the wall thickness of the steerable tube to ensure that the overall system maintains a low circumferential profile. In other embodiments, the securing element of the pull wire assembly may be laser welded to the medical instrument.

The devices, systems, and methods of this disclosure may be used for connected bronchial passageways of the lung. The devices, systems, and methods may also be suited for navigation and treatment of other tissues, via natural or surgically created connected passageways, in any of a variety of anatomical systems including the colon, the intestines, the kidneys, the brain, the heart, the circulatory system, or the like. The methods and embodiments of this disclosure are also suitable for non-surgical applications.

One or more elements in embodiments of the invention may be implemented in software to execute on a processor of a computer system such as control processing system 600. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device, The code segments may be downloaded via computer networks such as the Internet, Intranet, etc.

Note that the processes and displays presented may not inherently be related to any particular computer or other apparatus. Various general-purpose systems may be used with programs in accordance with the teachings herein, or it may prove convenient to construct a more specialized apparatus to perform the operations described. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A medical instrument comprising:
an anchoring element comprising a hollow cylindrical tube having an outer diameter;
a steerable tube comprising a plurality of grooves extending along a length of the steerable tube, wherein each groove of the plurality of grooves has an open cross-sectional shape, and wherein the anchoring element is disposed distal to a distal end of the steerable tube with a fixed position relative to the distal end of the steerable tube; and a plurality of pull wires each having a proximal end, a distal portion including a distal end, and a securing element fixedly secured to the distal portion, the securing element including an outer diameter sized smaller than the outer diameter of the anchoring element, the securing element being coupled to the anchoring element to prevent proximal translation of the distal end of a respective pull wire along a longitudinal axis of the medical instrument past the anchoring element, wherein each pull wire of the plurality of pull wires is at least partially disposed within a respective groove of the plurality of grooves.

2. The medical instrument of claim 1, wherein the securing element of at least one pull wire of the plurality of pull wires is fixedly secured to an outer surface of the anchoring element.

3. The medical instrument of claim 2, wherein the securing element of the at least one pull wire is soldered to the anchoring element.

4. The medical instrument of claim 3, further comprising an active flux, wherein the securing element of the at least one pull wire is soldered to the anchoring element using solder and the active flux.

5. The medical instrument of claim 2, wherein the securing element of the at least one pull wire is laser welded to the anchoring element.

6. The medical instrument of claim 1, wherein the securing element of at least one pull wire of the plurality of pull wires is Ni/Au plated.

7. The medical instrument of claim 1, wherein the securing element of at least one pull wire of the plurality of pull wires comprises a tubular crimp that circumferentially surrounds a portion of the distal portion of the at least one pull wire.

8. The medical instrument of claim 7, wherein the tubular crimp comprises a compressed tubular crimp fixedly secured to the distal portion of the at least one pull wire.

9. The medical instrument of claim 1, wherein at least one pull wire of the plurality of pull wires comprises a braided cable wire.

10. The medical instrument of claim 1, wherein at least one pull wire of the plurality of pull wires comprises a solid wire.

11. The medical instrument of claim 1, wherein the anchoring element has an inner diameter that is larger than an outer diameter of the steerable tube.

12. The medical instrument of claim 1, wherein the steerable tube is formed of shape memory material.

13. The medical instrument of claim 1, wherein each groove of the plurality of grooves has a U-shaped cross-sectional shape.

14. A medical instrument, comprising:

an anchoring element comprising a hollow cylindrical tube having an outer diameter;

a steerable tube comprising a lumen defining an inner surface and a wall surrounding the lumen, the wall including a wall thickness extending from the inner surface to an outer surface of the steerable tube, wherein the steerable tube includes a plurality of radially enclosed channels running within the wall, wherein the anchoring element is disposed distal to a distal end of the steerable tube with a fixed position relative to the distal end of the steerable tube; and a plurality of pull wires, wherein each pull wire of the plurality of pull wires is disposed within a respective channel of the plurality of channels and comprises a proximal end, a distal portion including a distal end, and a securing element fixedly secured to the distal portion, the securing element including an outer diameter sized smaller than the outer diameter of the anchoring element, the securing element being coupled to the anchoring element to prevent proximal translation of the distal end of a respective pull wire along a longitudinal axis of the medical instrument past the anchoring element.

15. The medical instrument of claim 14, wherein a proximal surface of the securing element of at least one pull wire of the plurality of pull wires is attached to the distal end of the steerable tube.

16. The medical instrument of claim 15, wherein the proximal surface of the securing element of the at least one pull wire is soldered to the distal end of the steerable tube.

17. The medical instrument of claim 15, wherein the proximal surface of the securing element of the at least one pull wire is laser welded to the distal end of the steerable tube.

18. The medical instrument of claim 14, wherein the outer diameter of the securing element of at least one pull wire of the plurality of pull wires is sized less than or equal to the wall thickness of the steerable tube.

19. A medical instrument, comprising:

an anchoring element comprising a hollow cylindrical tube having an outer diameter;

a steerable tube, wherein the anchoring element is disposed distal to a distal end of the steerable tube with a fixed position relative to the distal end of the steerable tube; and a plurality of pull wires each having a proximal end, a distal portion including a distal end, and a securing element secured to and disposed around the distal portion, the securing element including an outer diameter sized smaller than the outer diameter of the anchoring element, the securing element being coupled to the anchoring element to prevent proximal translation of the distal end of a respective pull wire along a longitudinal axis of the medical instrument past the anchoring element.

20. The medical instrument of claim 19, wherein at least one pull wire of the plurality of pull wires is secured to the anchoring element only indirectly by its respective securing element.

* * * * *